United States Patent [19]

Welsh et al.

[11] Patent Number: 4,914,034

[45] Date of Patent: Apr. 3, 1990

[54] DISPOSABLE BIOLOGICAL INDICATOR TEST PACK FOR MONITORING STEAM AND ETHYLENE OXIDE STERILIZATION CYCLES

[75] Inventors: Jon D. Welsh, Fairview; Denis G. Dyke, Edinboro, both of Pa.

[73] Assignee: American Sterilizer Company, Erie, Pa.

[21] Appl. No.: 288,362

[22] Filed: Dec. 22, 1988

Related U.S. Application Data

[63] Continuation-in-part of Ser. No. 50,585, May 15, 1987, Pat. No. 4,839,291.

[51] Int. Cl.⁴ .......................... C12Q 1/22; C12M 1/16
[52] U.S. Cl. ..................... 435/296; 435/31; 435/299; 435/311; 206/305; 206/569
[58] Field of Search ............ 435/31, 311, 293, 295, 435/296, 287, 299, 292; 206/305, 569

[56] References Cited

U.S. PATENT DOCUMENTS

| | | | |
|---|---|---|---|
| 3,474,003 | 10/1969 | Hirsch | 435/296 |
| 3,661,717 | 5/1972 | Nelson | 435 L/296 X |
| 3,712,743 | 8/1973 | Hewshrlwood | 435/287 |
| 4,291,122 | 9/1981 | Orelski | 435/296 X |
| 4,304,869 | 12/1981 | Dyke | 435/296 |
| 4,579,823 | 4/1986 | Ryder | 435/296 |
| 4,591,566 | 5/1986 | Smith | 435/291 |
| 4,596,696 | 6/1986 | Scoville, Jr. | 435/31 X |
| 4,596,773 | 6/1986 | Wheeler | 435/296 |
| 4,636,472 | 1/1987 | Bruse | 435/287 X |
| 4,717,661 | 1/1988 | McCormick et al. | 435/296 X |

OTHER PUBLICATIONS

"Good Hospital Practice: Steam Sterilization and Sterility Assurance (Proposed Revision)" selected pages, AAMI Recommended Practice (Nov. 1986 Revision Draft).

"Good Hospital Practice: Performance Evaluation of Ethylene Oxide Sterilizers–Ethylene Oxide Test Packs", Association for the Advancement of Medical Instrumentation (Feb. 11, 1985).

Assert TM –Product insert for Steam and Ethylene Oxide Sterilization Test Packs.

"Assert TM –Single-Use Biological Test Pack· Steam Performance Studies", Technical Report 86-4, Surgicot.

"Assert TM –Single-Use Ethylene Oxide (EO) Biological Test Pack, EO Performance Study" Technical Report, 86-5, Surgicot.

Propper Bio Challenge Test-Pak for Steam Sterilization–Advertising sheet.

ATI product insert for Steam Sterilization Test Pack.

*Primary Examiner*—Larry Jones
*Attorney, Agent, or Firm*—Kirkpatrick & Lockhart

[57] ABSTRACT

Disposable test packs for monitoring the efficacy of steam or ethylene oxide sterilization cycles includes a fiber board housing for a biological indicator. The housing includes two end sections and a midsection. Each end section includes an outer tube and a longer inner tube. The open end of the outer tubes abut the opposing open ends of the midsection to define a seam or gap. The inner tube extends past the seam and telescopes into the midsection. The seam and the close tolerance between the inner tube and the midsection provide a tortuous path for the entry of sterilant into the interior of the housing. The tortuous path has a moisture absorbent surface and is dimensioned to promote intimate contact between the sterilant and the absorbent surface. A second path of entry is provided in the embodiment adapted for use in monitoring ethylene oxide sterilization processes only. A midsection can be made of a transparent, sterilant impermeable material to permit observation of the interior of the housing.

18 Claims, 5 Drawing Sheets

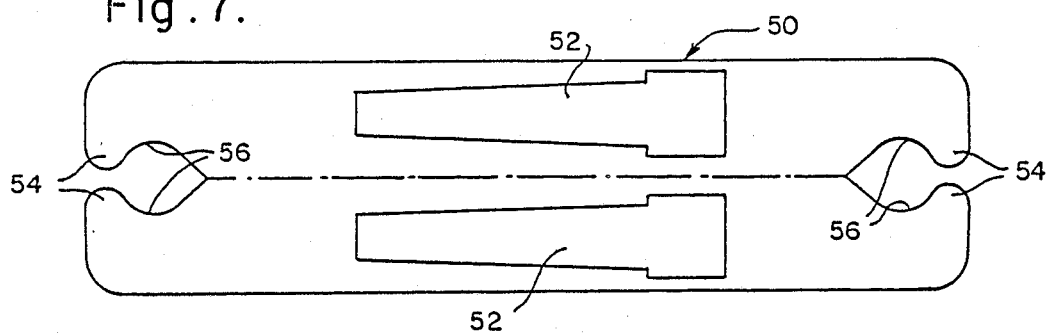
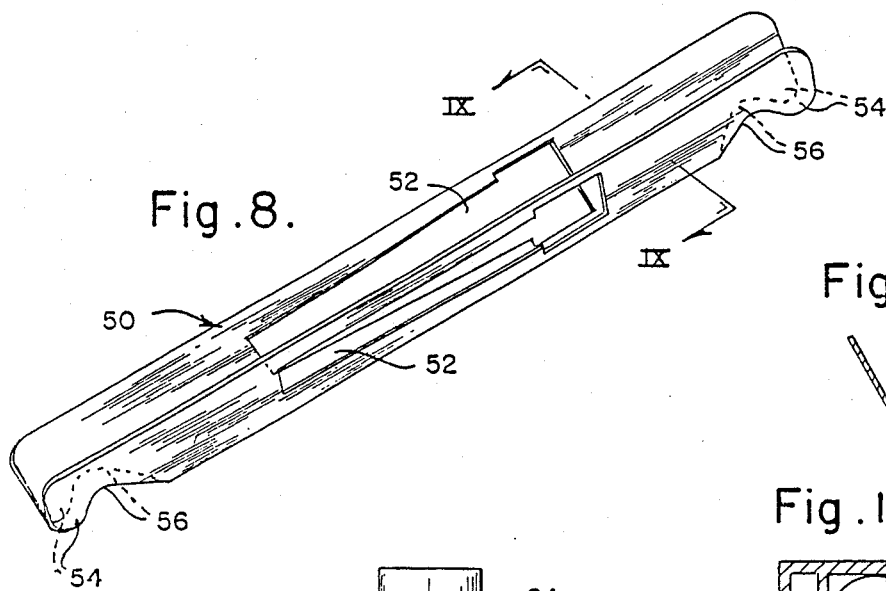
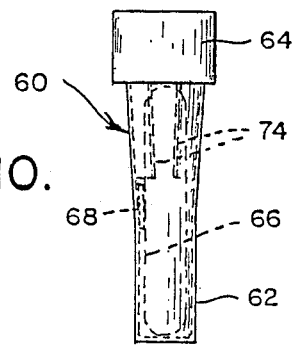
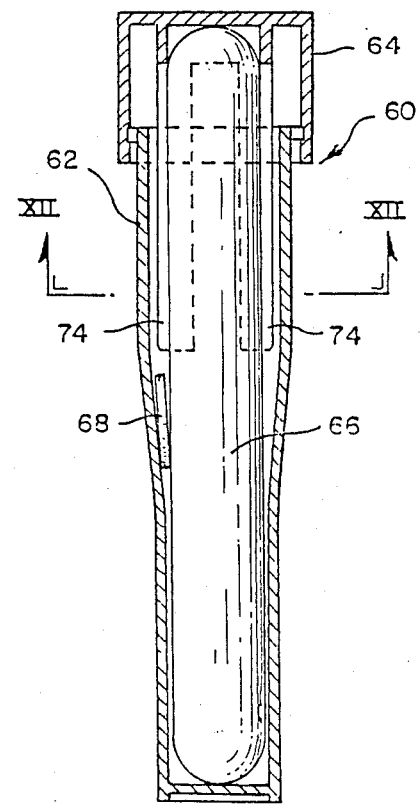
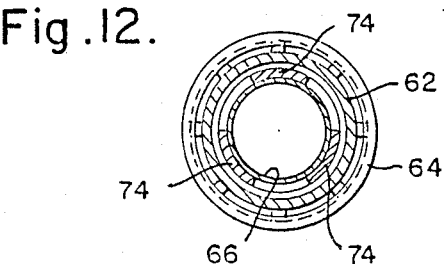

DISPOSABLE BIOLOGICAL INDICATOR TEST PACK FOR MONITORING STEAM AND ETHYLENE OXIDE STERILIZATION CYCLES

This is a continuation-in-part of co-pending U.S. patent application Ser. No. 050,585 filed on May 15, 1987 now U.S. Pat. No. 4,839,291, issued Jun. 13, 1989.

BACKGROUND OF THE INVENTION

1. Field of the Invention

The present invention relates to apparatus for monitoring steam and ethylene oxide sterilization cycles.

2. Description of the Prior Art

A variety of means are available for monitoring the efficacy of sterilization cycles. Standardized spores of a strain sufficiently resistant to the sterilization medium are placed on a substrate and are exposed to the sterilization process. Sterilization of the standardized spore strain provides a high degree of confidence that sterilization of bacterial strains in the chamber load has occurred. Conversely, survival of the standardized spore stain indicates unsatisfactory sterilization of the load. The Association for the Advancement of Medical Instrumentation (AAMI) has published recommendations for evaluating both ethylene oxide and steam sterilizers. Test packs containing biological indicators and other materials are intended to challenge all of the parameters necessary for ethylene oxide or steam sterilization. In actual chamber loads, it may take several minutes into the sterilization cycle before the load is sufficiently exposed to sterilant for sterilization of the load to occur. The test packs should not be sterilized prior to the sterilization of the load. One requirement of a test pack, therefore, is to impede the flow of sterilant to the biological indicator to more closely simulate the rate of sterilization experienced by the load.

Biological indicators are defined by AAMI as a calibration of microorganisms of high resistance to the mode of sterilization being monitored, placed in or on a substrate, packaged to maintain the integrity of the inoculated substrate in a manner convenient to the ultimate user, which serve to demonstrate that sterilization conditions were met. The foregoing definition of biological indicators shall be adopted for purposes of the instant application.

A biological indicator for monitoring the efficacy of ethylene oxide sterilization typically includes *Bacillus subtilis* spores. A biological indicator for monitoring the efficacy of steam sterilization typically includes *Bacillus stearothermophilus* spores. However, any microorganism which is highly resistant to the particular sterilization medium will suffice. Vegetative bacteria are known to be easily killed by steam and, thus, are not recommended. Thermotolerant organisms, such as Bacillus spores are known to be extremely resistant. The challenge organism should be more resistant to the sterilant and the population should be greater than the bioburden of the chamber load.

For qualification testing of an ethylene oxide sterilizer, AAMI recommends placing a biological indicator into the barrel of a plastic syringe so that the diaphragm of the plunger does not touch the indicator. The needle end of the syringe must be open. A plastic airway, a length of latex tubing and two such syringes are placed in the center of a stack of folded surgical towels. The stack is then wrapped in a wrapping material. The resulting test pack is designed to challenge the parameters of ethylene oxide sterilization. The towels act as moisture and ethylene oxide absorbents and as a heat sink, the latex and plastic tubes act as ethylene oxide absorbents, and the plastic syringes act as heat sinks, ethylene oxide absorbents and a means for impeding the flow of sterilant to the biological indicators. The biological indicators provide the microbial challenge.

The heat sinks are necessary to provide a thermal challenge to the sterilization process. The test pack and, particularly, the environment surrounding the biological indicator should simulate the thermal profile of the normal chamber load. The heat sinks act to slow down the transfer of heat to the spores. In the ethylene oxide application, the additional parameters of humidity and ethylene oxide permeation are equally, if not more, important.

Recommended means for routinely monitoring ethylene oxide sterilization is to wrap the syringe and biological indicator described above in a clean huck towel and seal them in a standard peel pouch. One commercially available monitor includes a plastic syringe which contains a biological indicator and a stack of filter paper discs within the barrel of the syringe. The discs are disposed between the open needle end of the syringe and the biological indicator. The biological indicator includes a plastic ampule with a cap. The cap has a hole in the center to permit the sterilant to enter. A vial of growth media and a spore strip are enclosed in the ampule. Following the sterilization cycle, the ampule is squeezed to break the vial to immerse the spore strip in growth media. The barrel of the syringe is enclosed in a fiber board tube. A chemical process indicator to indicate exposure to ethylene oxide gas is disposed on the fiber board tube. The syringe is placed in a standard peel pouch having a clear plastic sheet heat sealed to a medical grade paper backing which is permeable to the sterilant.

A variety of similar ethylene oxide monitors are commercially available. All are designed to monitor only ethylene oxide sterilization cycles.

A problem sometimes encountered in steam sterilization is air entrapment. Cool air pockets can insulate portions of the load preventing exposure to the sterilant. Very small amounts of air do not impede sterilization as long as the air and steam are thoroughly mixed. When steam contacts cooler objects, the objects absorb the latent heat of the steam, the steam collapses, condensate collects on the objects and any air present remains. Additional steam is drawn to the area and the process is repeated so that air is accumulated and compressed into cool air pockets. Various devices are available to detect critical quantities of air in steam sterilizers. The test packs used to monitor the efficacy of steam sterilization are not designed as air detectors but should be sensitive to air which impedes sterilization. The environment to which the biological indicators are exposed should simulate the sterilizer environment.

The AAMI recommendations for monitoring the efficacy of steam sterilization cycles include using a packaging material which allows adequate air removal to avoid the disproportionate accumulation of air around the biological indicator. The material must also allow steam penetration of the package contents and should provide an adequate barrier to microorganisms. The recommendations for a test pack for use in both gravity-displacement and prevacuum sterilizers include using an appropriate biological indicator in a 16 towel test pack. The towels are folded and stacked. The biological indicator should be placed between the 7th and 8th towels in the geometric center of the pack.

A commercially available test pack consists of a small clear plastic tube containing a biological indicator and a chemical process indicator strip. The tube is closed by two plastic caps. A hole at the end o each cap vents the tube and permits the entry of sterilant. Cotton filled gauze covered sponges inside the tube provide means for loosely maintaining the biological and chemical indicators in the midsection of the tube. Loose fitting water-repellent foam discs are disposed at each end of the tube adjacent to the holes in the caps. The dual vent system provided by the opposing holes in the caps is said to mimic the characteristic resistance of the AAMI recommended 14-towel test pack to removal of air by prevacuum or gravity-displacement sterilizer air removal methods. The disposable test pack described is designed for use with steam sterilizers only.

Another type of commercially available steam monitoring test pack, also adapted for use in monitoring only steam sterilization cycles, comprises a stack of filter paper. A cavity is cut out of the center of the stack to house a biological indicator. One manufacturer then wraps the stack of filter paper in a surgical grade paper wrap. Another places the stack in a box. Sterilant entry is from five sides of the stack of filter paper.

A problem with the AAMI recommended procedures is reproducibility from test pack to test pack due to the differences in the quality of towels used and the variance in technique of the persons preparing the test packs. The commercially prepared test packs attempt to standardize the test packs.

An object of the present invention is to provide a single, standardized test pack for use in monitoring the efficacy of both steam and ethylene oxide sterilization cycles. A further object of the present invention is to provide such a test pack which provides a monitor of both steam and ethylene oxide sterilization cycles having the same degree of challenge as the test packs recommenced by AAMI.

SUMMARY OF THE INVENTION

The present invention provides two embodiments of a test pack which represents a sterilant penetration, thermal and microbial challenge to steam sterilization or ethylene oxide processes; monitors the efficacy of such processes; and provides a reliable, reproducible standard for testing the efficacy of such processes. The test pack of the present invention includes a housing having an interior made at least in part of a material having heat sink, insulating and moisture absorbent properties. The housing material in the embodiment designed for use with ethylene oxide sterilization processes is also ethylene oxide absorbent. The material is preferably a cellulosic material, such as fiber board. The housing in both embodiments also includes a section made of a transparent material to permit observation of a biological indicator within the housing. The housing is configured to define at least one tortuous path for providing entry of sterilant into the housing. This tortuous path has a moisture absorbent surface and is dimensioned to promote intimate contact between the sterilant and the absorbent surface. In the ethylene oxide sterilization embodiment, a second path of entry into the housing is provided. The second path may be a hole in one end of the housing.

The test pack also includes a biological indicator which offers a microbial challenge resistant to sterilization by steam sterilants in one embodiment and by ethylene oxide sterilants in the other embodiment. Means, preferably a carrier, are provided to position the biological indicator within the housing. The carrier for positioning the biological indicator has a cutout section for holding the biological indicator and shock absorbing means at its ends.

The housing is comprised of two end sections and a midsection positioned between the end sections. The midsection has two open ends. Each end section has an inner member and an outer member. Each outer member has one open end in a substantially abutting relationship with one of the open ends of the midsection to define a seam therebetween. The inner member of each end section telescopes into its corresponding outer member and into a portion of the midsection through the open ends to define the tortuous paths which progress through the seam, between the outer surface of the inner member and the inner surface of the portion of the midsection and into the housing. The seam may be covered with a layer of material, such as medical grade paper, which is permeable to steam.

BRIEF DESCRIPTION OF THE DRAWINGS

The present invention will be better understood by reference to the drawings in which:

FIG. 7 is a plan view of the carrier of FIG. 5;

FIG. 8 is an isometric view of the carrier;

FIG. 9 is a sectional view of the carrier along the line IX—IX of FIG. 8;

FIG. 10 is a side elevation view of the biological indicator;

FIG. 11 is a sectional view of the biological indicator of FIG. 10;

FIG. 12 is a sectional view of the biological indicator along the line XII—XII of FIG. 11;

DETAILED DESCRIPTION OF THE PREFERRED EMBODIMENT

Figure 16:
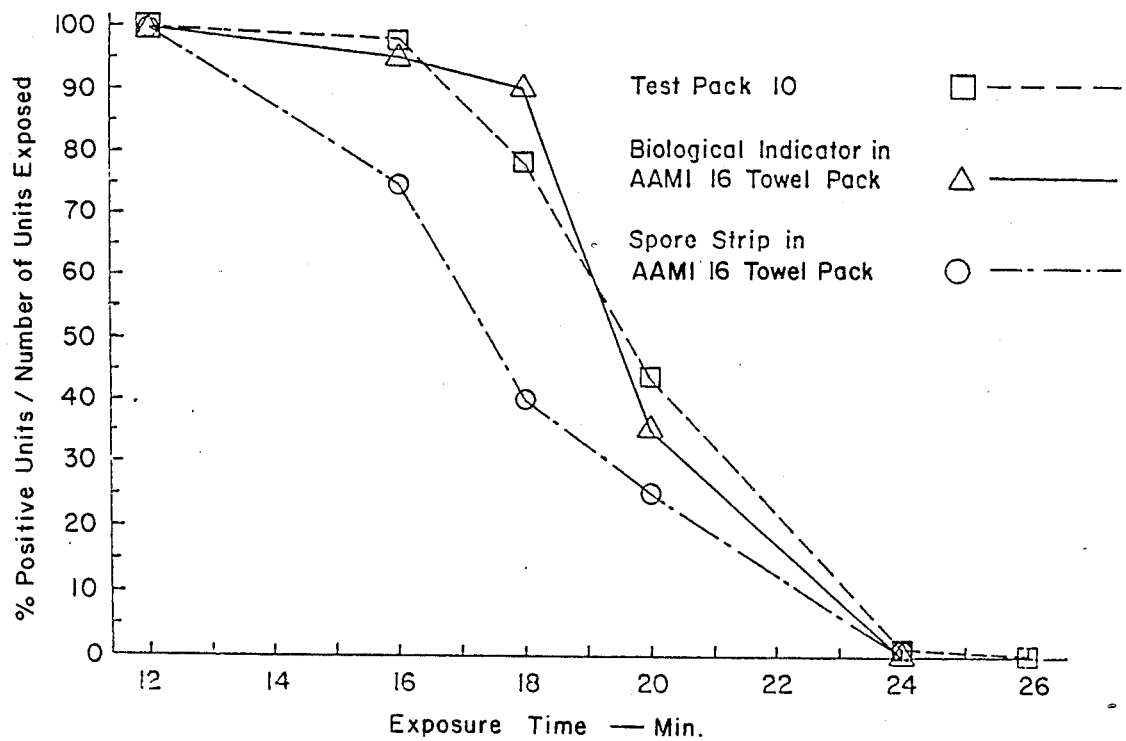
Figure 17:
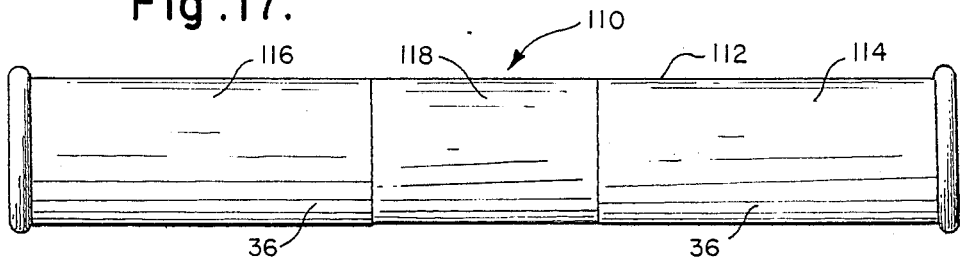
FIG. 17 is a side elevation view of the test pack of the present invention for use in monitoring steam sterilization processes.
Figure 18:
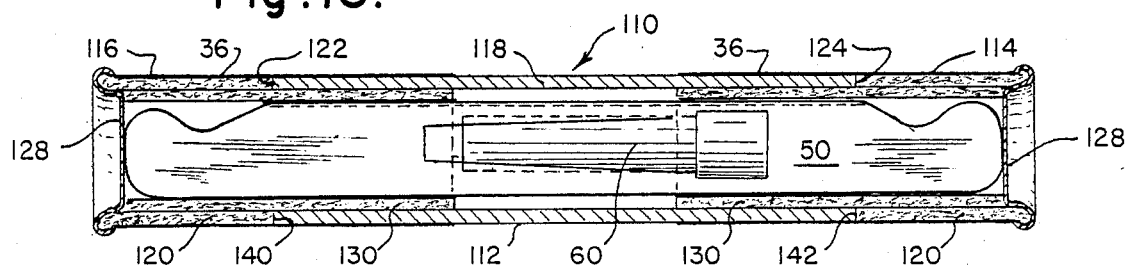
FIG. 18 is a sectional view of the test pack of FIG. 17.
Figure 19:
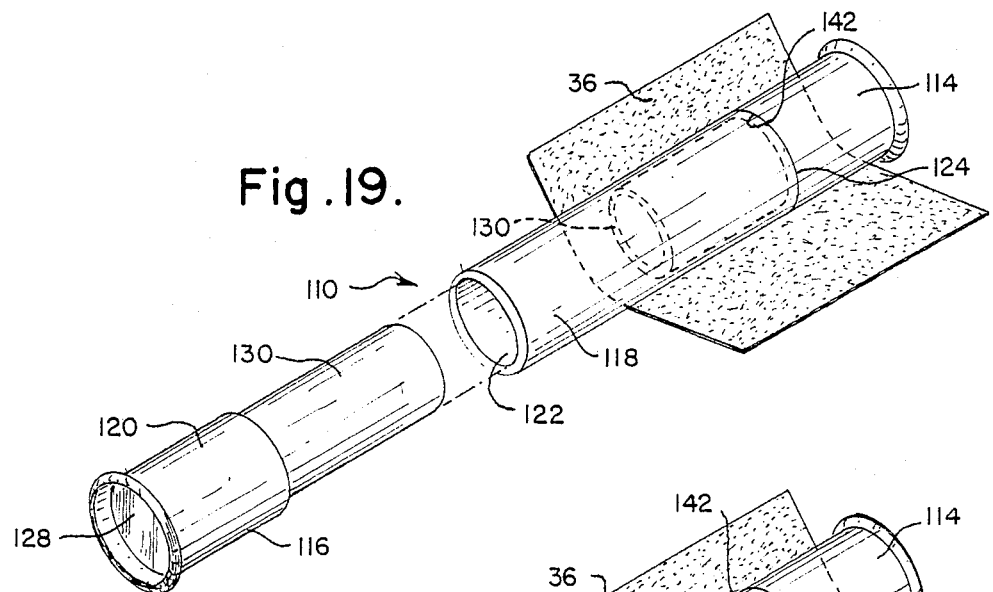
FIG. 19 is an isometric view of an opened test pack of FIG. 17.
Figure 20:
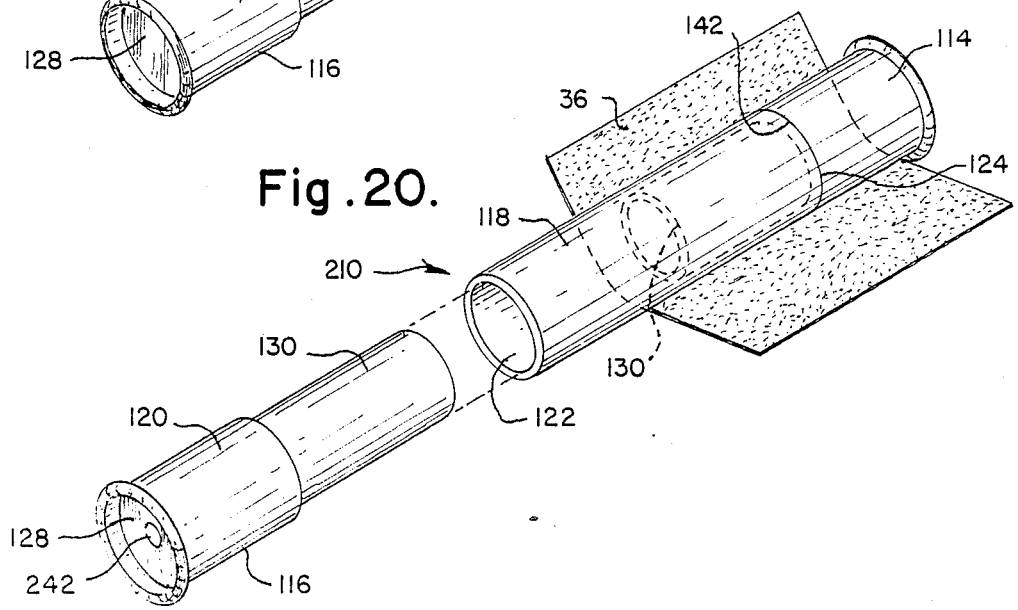
FIG. 20 is an isometric view of the test pack of the present invention for use in monitoring ethylene oxide sterilization processes.

The test pack 10 of the present invention, as shown in FIGS. 1-4, provides a single, disposable device for monitoring the efficacy of either a steam or an ethylene oxide sterilization cycle. FIGS. 17 through 19 illustrate the preferred embodiment of test pack 110 for use in monitoring the efficacy of a steam sterilization cycle alone. FIG. 20 illustrates the preferred embodiment of test pack 210 for use in monitoring the efficacy of an ethylene oxide sterilization cycle alone. FIGS. 5 through 12 are applicable to all embodiments of the test packs 10, 110 and 210. As demonstrated by the test data represented hereinbelow and in the graphs of FIGS. 13 through 16, the test packs 10, 110 and 210 provide an easy to use sterilization monitor which performs in accordance with the AAMI recommendations for both steam and ethylene oxide sterilization cycles or for steam or ethylene oxide sterilization cycles alone.

Test pack 10 includes generally a housing 12, a biological indicator 60 and means 50 for maintaining the position of biological indicator 60 within housing 12. The housing 12 is constructed of a moisture and ethylene oxide absorbent, insulating cellulosic material, such as fiber board.

Housing 12 includes an outer member, or tube 20 and an inner member, or tube 30. Outer tube 20 has an upper portion 22 open at one end and a lower portion 24, also open at one end.

Figure 1:
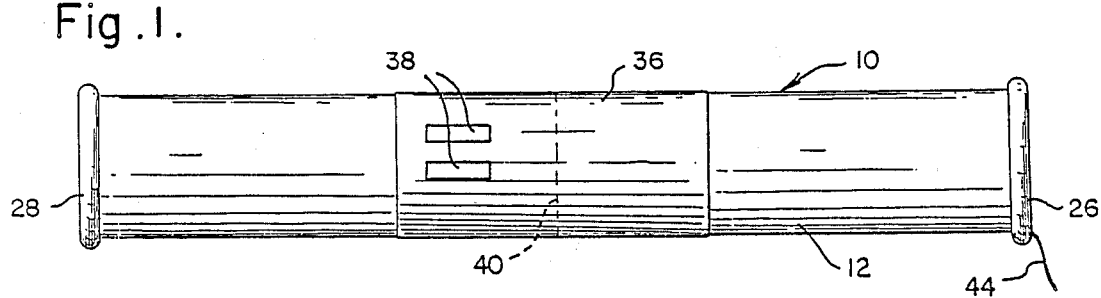
FIG. 1 is a side elevation view of the test pack of the present invention for use in monitoring both steam and ethylene oxide sterilization processes.
Figure 2:
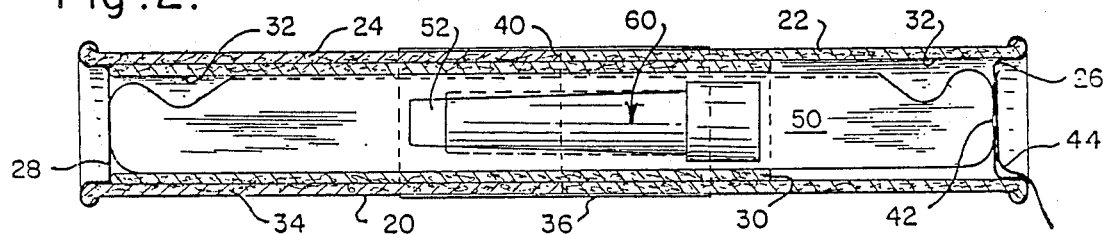
FIG. 2 is a sectional view of the test pack of FIG. 1.
Figure 3:
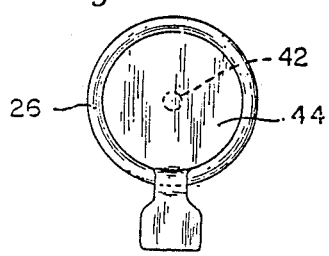
FIG. 3 is an end view of the test pack of FIG. 1.
Figure 4:
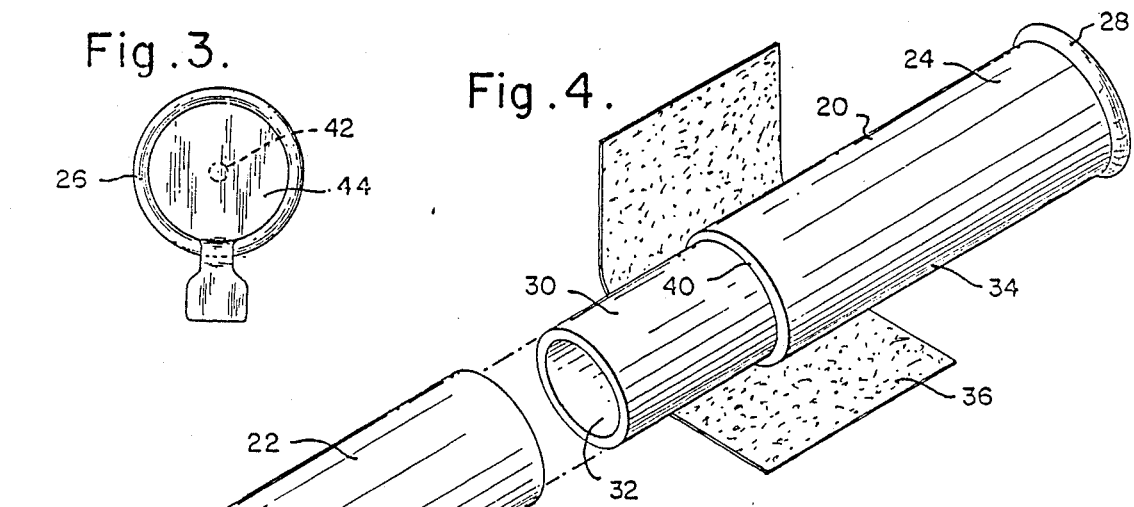
FIG. 4 is an isometric view of an opened test pack of FIG. 1.
Figure 5:
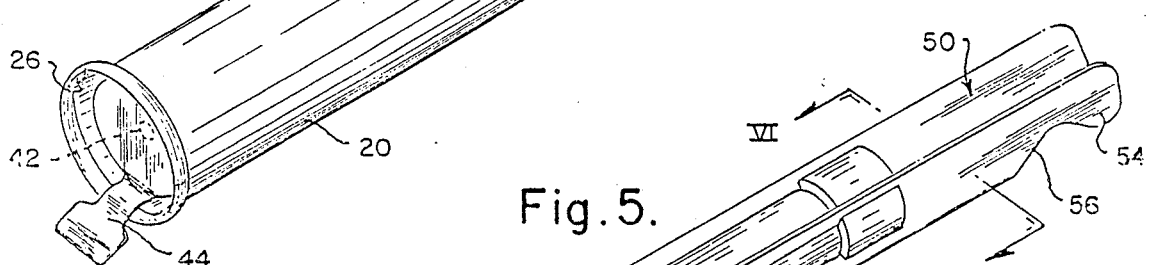
FIG. 5 is an isometric view of the carrier and the biological indicator of the present invention.
Figure 6:
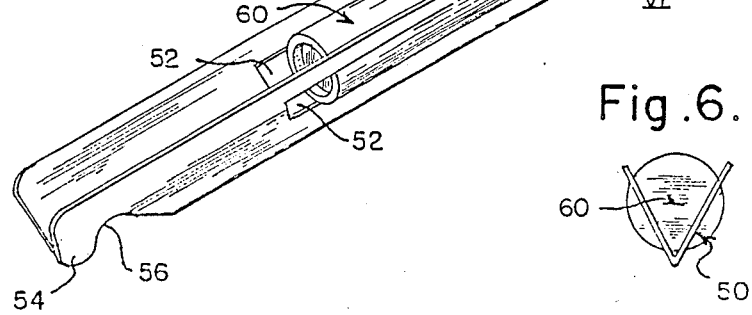
FIG. 6 is a sectional view of the carrier and the biological indicator taken along the line VI—VI in FIG. 5.

Housing 12 has at least one tortuous path for entry of sterilant into its interior. In the preferred embodiment, a seam, or gap 40 is defined between the open ends of upper and lower portions 22, 24 of the outer tube 20. The open ends are preferably in substantially abutting relationship to define seam 40 therebetween, but they need not touch. As shown in FIG. 2, inner tube 30 telescopes into the full depth of lower portion 24 and telescopes part way into upper portion 22. Inner tube 30 may, however, telescope only part way into lower portion 24 also. The outer surface of inner tube 30 is preferably smooth to permit an easy sliding contact between the exterior of inner tube 30 and the interior of the upper portion 22 of outer tube 20. The smooth surface aids in assembly and disassembly. There is a relatively close tolerance between the inner tube 30 and the upper and lower portions 22, 24 so that at least one, but, if desired, two tortuous paths may be defined which progress through the seam 40 between the interior of upper portion 22 and the exterior of inner tube 30 into housing 12 and/or through seam 40 between the interior of lower portion 24 and the exterior of inner tube 30 into housing 12. The tortuous paths impede the flow of sterilant into the interior of housing 12 to satisfy the AAMI recommendations and more closely simulate actual sterilization parameters. While two or more such tortuous paths are possible, at least one such tortuous path into housing 12 will suffice. For example, inner tube 30 may be sealed in any suitable manner to one of upper or lower portions 22, 24 to provide only one tortuous path through seam 40 to the interior of housing 12 so that unidirectional flow of sterilant into housing 12 is provided.

Upper portion 22 has a closed end 26. A hole 42 in end 26 is covered with an adhesive backed tab 44 which is impermeable to steam. Tab 44 permits the optional opening or closure of hole 42. Tab 44 seals hole 42 when test pack 10 is used to monitor steam sterilization cycles and is removed when test pack 10 is to be used to monitor ethylene oxide sterilization cycles. When in place, tab 44 seals hole 42 to prevent the entry of sterilant therethrough. The closed end 28 of lower portion 24 does not include a hole similar to that in end 26.

The outer surfaces of upper and lower portions 22, 24 may be lined with foil 34 or any other suitable means for making outer tube 20 nonabsorbent and impervious to sterilant penetration. Unless tab 44 is removed, entry of the sterilant is permitted only through seam 40 along the tortuous path or paths described above. In the preferred embodiment of test pack 10 a sterilant permeable layer 36, such as medical grade paper, preferably covers the entire outer tube 20 and, at least, seam 40. Sterilant permeates the layer 36 to enter the test pack 10 through seam 40. A chemical process indicator 38 and any desired labeling information may be printed on the layer 36. The chemical indicator 38 may be any suitable known indicator which will demonstrate whether the test pack 10 has been exposed to either steam or ethylene oxide sterilization conditions. Because different chemicals are required to indicate exposure to each type of sterilant, both chemicals are imprinted on the layer 36. Alternatively, a chemical indicator strip may be placed inside the housing 12.

The interior surfaces 32 of tubes 20 and 30 are not lined or coated. The exposed hydrophilic fiber board material acts as an absorbent for moisture present in both steam and ethylene oxide sterilization cycles, and as a heat sink to absorb the latent heat of the sterilant to slow the transfer of heat to the biological indicator 60. The fiber board is also absorbent to ethylene oxide.

Biological indicator 60 may be any suitable known biological indicator carrying microorganisms which are highly resistant to steam and ethylene oxide sterilization cycles. The preferred microorganisms are spores of Bacillus subtilis and spores of Bacillus stearothermophilus.

Biological indicator 60 includes an open ended ampule 62, a cap 64 adapted to enclose the open end of ampule 62 so that an annular space is defined between the interior surface of the cap 64 and the exterior surface of the ampule 62. A second tortuous path 70 is thus defined by the annular space into the interior of the ampule 62. A vial 66 of growth media, such as trypticase soy broth and a pH indicator dye, and a substrate 68 for the sterilization resistant microorganisms are enclosed in the ampule 62. Prongs 74 extend downwardly form cap 64 into ampule 62 to hold the vial 66 in place. Cap 64 has two positions. The first position permits the tortuous path 70 to remain open to admit the sterilant. The second position presses cap 64 downwardly to close the open end of ampule 62 and to press prongs 74 down over vial 66 to wedgedly engage vial 66 and thereby cause vial 66 to rupture. A preferred ampule is described in more detail in Dyke U.S. Pat. No. 4,304,869 which is hereby incorporated herein by reference. A second chemical process indicator may be imprinted on the outer surface of ampule 62 to indicate whether the ampule 62 has been exposed to either sterilant.

The means, such as carrier 50, for maintaining the position of biological indicator 60, is preferably made of plastic and includes a cut out section 52 into which biological indicator 60 is seated, cutaway portions 56 at each end and tips 54 adjacent to the cutaway portions 56. The tips 54 and cutaway portions 56 act as shock absorbers during shipping. Cutaway portions 56 also provide a convenient means for removing carrier 50 and biological indicator 60 from housing 12 at the conclusion of a sterilization cycle.

The fiber board material of housing 12 acts as a heat sink, a moisture and ethylene oxide absorbent and as an insulator to prevent the rapid warm up of the biological indicator. As indicated previously, the intent of test pack 10 is to provide a sterilant penetration, thermal and microbial challenge to both kinds of sterilization processes. The sterilization environment experienced by the most difficult to sterilize component of a chamber load must be simulated in the environment to which the spores on substrate 68 are exposed. The time required to kill the spores on substrate 68 should at least equal and preferably surpass the time required to kill microorganisms in the chamber load. Accordingly, means for slowing the rate at which the sterilant reaches the substrate 68 are provided by the tortuous paths, the heat sink, insulating and moisture absorbent properties of the fiber board, the ethylene oxide absorbent properties of the fiber board and the plastic carrier 50 and the heat sink properties of the cool liquid growth media in vial 66.

The design of test pack 10 of the present invention provides at least one tortuous path of sterilant flow toward the substrate 68. Steam, for example, enters through layer 36, seam 40, between inner tube 30 and the interior surface of upper portion 22 (and/or the interior surface of lower portion 24) into the interior of housing 12, then toward biological indicator 60 and the second tortuous path 70 defined by cap 64 and ampule 62 to substrate 68. Following removal of the tab 44, ethylene oxide enters through hole 42, and to a lesser extent through the path provided for the entry of steam. The ethylene oxide reaches the second tortuous path 70 and flows toward substrate 68.

The sterilant flow along the moisture absorbent surface of the tortuous path into housing 12 provided by test pack 10 of the present invention aids in sensitizing the device to the presence of noncondensable gases, such as air, into the sterilant. When, for example, steam comes in contact with the fiber board interior 32 along the tortuous path into housing 12, the latent heat from the steam is absorbed into the fiber board causing the steam to collapse. The condensate is then absorbed into the fiber board, leaving any air mixed with the steam remaining. The collapse of the steam draws in more steam which forces the air, if any, into housing 12. The air, if present, will enter ampule 60 to simulate the steam/air mix present in the sterilizer.

Test packs were prepared for steam and ethylene oxide sterilization cycles according to the AAMI recommendations for such test packs. Two biological indicators 60 and two spore strips enclosed in a glassine envelope were placed in each AAMI type test pack. Test packs 10 of the present invention and the appropriate AAMI type test packs were exposed, side by side, to steam and ethylene oxide sterilization cycles at varying times to develop a resistance profile for each test pack. All test results are expressed as percent positive units/no. of units exposed for each exposure time and sterilization cycle type.

Figure 13:
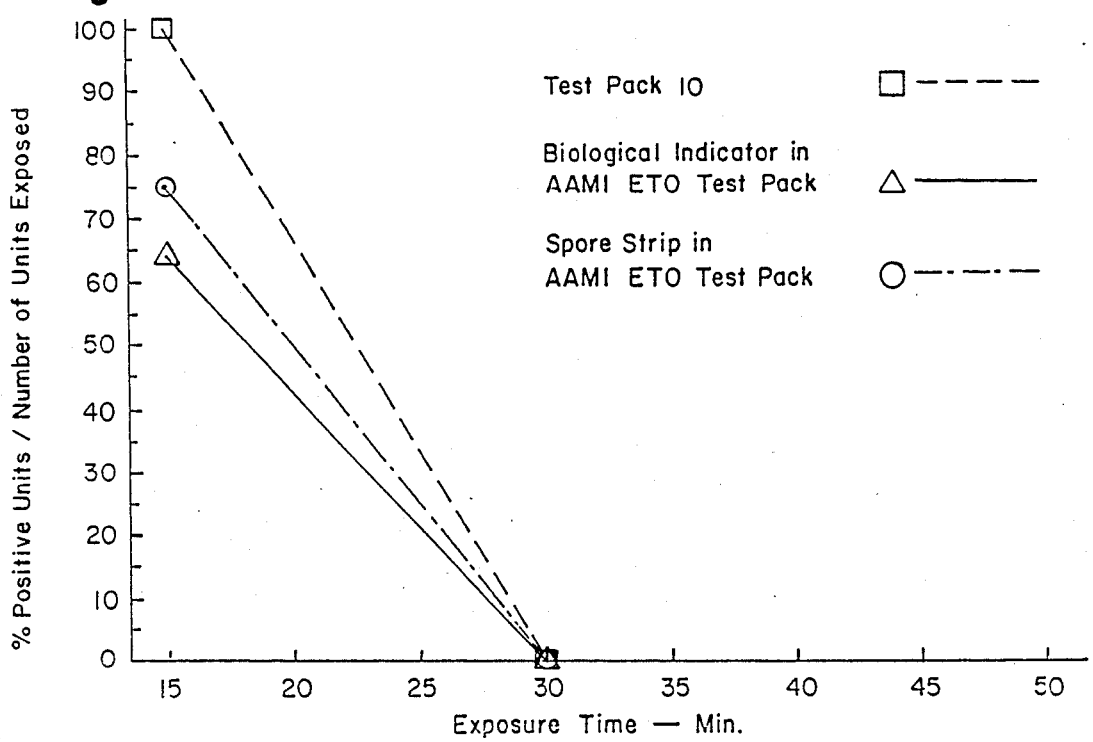
FIGS. 13 and 14 are graphs illustrating the results of comparative tests of the test packs of the present invention and AAMI recommended test packs in ethylene oxide sterilizers.

In a first series of tests, 120 test packs 10 per exposure were tested with AAMI packs in a 20×20×38 ethylene oxide sterilizer at 130~ F, 60% relative humidity and 600 mg ethylene oxide per liter ±10%. The results are illustrated in FIG. 13, and in Table I below.

TABLE I

| Exposure Time (min) | Test Pack 10 (%) | AAMI Test Packs | |
|---|---|---|---|
| | | Bio Indicator 60 (%) | Spore Strip (%) |
| 15 | 100 | 64 | 75 |
| 30 | 0 | 0 | 0 |
| 40 | 0 | 0 | 0 |
| 50 | 0 | 0 | 0 |

Figure 14:
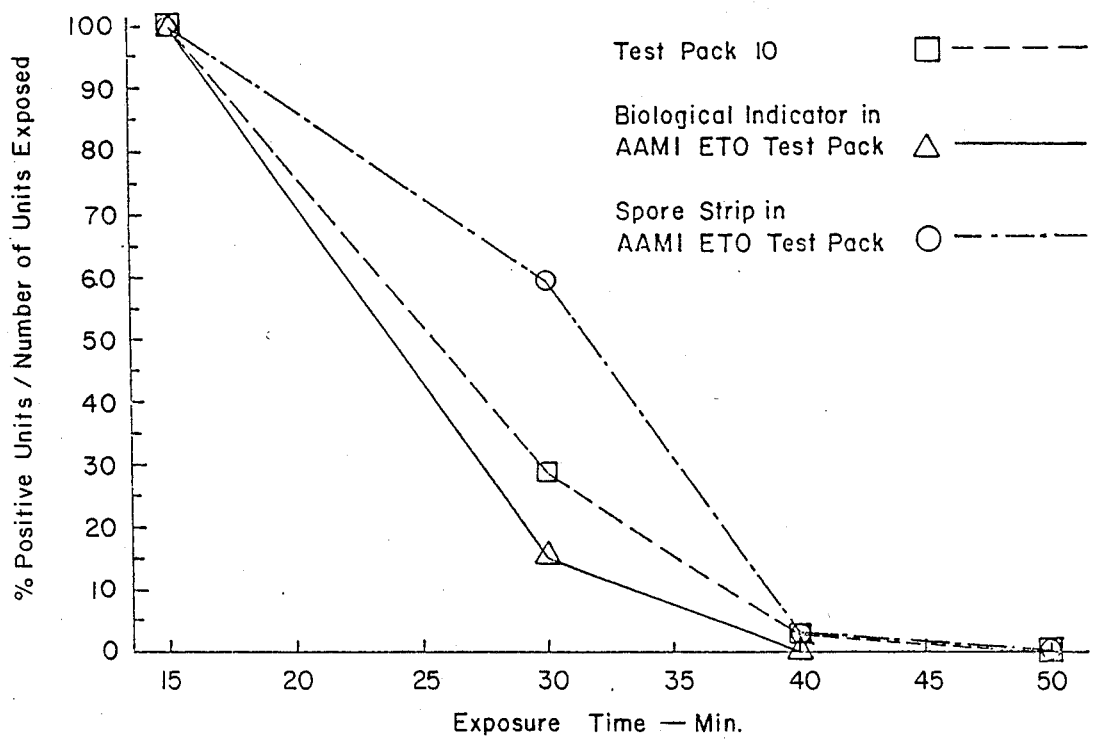

In a second series of tests, 70 test packs 10 per exposure were exposed to ethylene oxide sterilization cycles side by side with AAMI test packs in a Biological Indicator Evaluation Resistometer at 130~ F, 60% relative humidity and 600 mg ethylene oxide per liter ±10%. The results are shown in FIG. 14 and in Table II below.

TABLE II

| Exposure Time (min) | Test Pack 10 (%) | AAMI Test Packs | |
|---|---|---|---|
| | | Bio Indicator 60 (%) | Spore Strip (%) |
| 15 | 100 | 100 | 100 |
| 30 | 28.6 | 15.6 | 59.4 |
| 40 | 2.8 | 0 | 3.0 |
| 50 | 0 | 0 | 0 |

Figure 15:
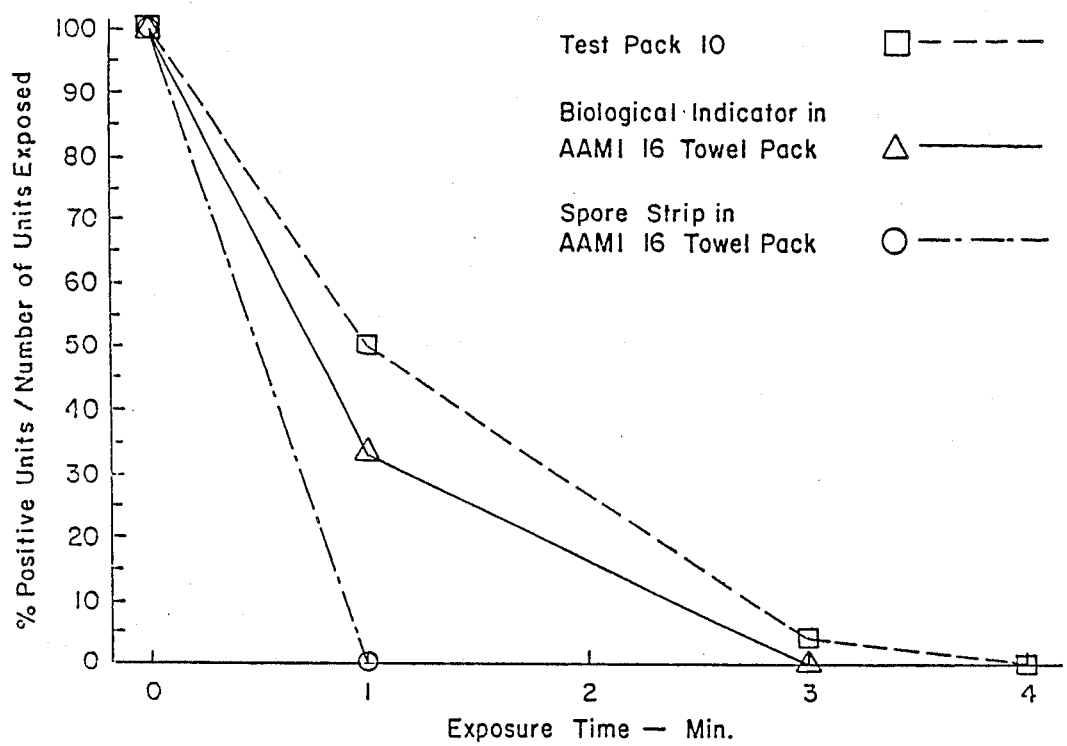
FIGS. 15 and 16 are graphs illustrating the results of comparative tests of the test packs of the present invention and AAMI recommended test packs in steam sterilizers.

In a third series of tests, 140 test packs 10 per exposure were tested with AAMI 16 towel test packs in a 270~ F prevacuum steam sterilizer. The results are shown in FIG. 15 and in Table III below.

TABLE III

| Exposure Time (min) | Test Pack 10 (%) | AAMI Test Packs | |
|---|---|---|---|
| | | Bio Indicator 60 (%) | Spore Strip (%) |
| 0 | 100 | 100 | 100 |
| 1 | 50 | 33 | 0 |
| 3 | 4.3 | 0 | 0 |
| 4 | 0 | 0 | 0 |

In a fourth series of tests 170 test packs 10 per exposure were tested with AAMI 16 towel test packs in a 250~ F gravity displacement steam sterilizer. The results are shown in FIG. 16 and in Table IV below.

TABLE IV

| Exposure Time (min) | Test Pack 10 (%) | AAMI Test Packs | |
|---|---|---|---|
| | | Bio Indicator 60 (%) | Spore Strip (%) |
| 12 | 100 | 100 | 100 |
| 16 | 97.0 | 95.0 | 75.0 |
| 18 | 78.2 | 90.0 | 40.0 |
| 20 | 43.5 | 35.0 | 25.0 |
| 24 | 1.0 | 0 | 0 |
| 26 | 0 | 0 | 0 |

A comparison of test pack 10 of the present invention to test packs recommended by AAMI for steam and ethylene oxide sterilization monitoring in a few different types of sterilizers demonstrates that test pack 10 functions in accordance with the AAMI recommendations for both steam and ethylene oxide sterilization cycles.

The test pack 10 provides an economical, disposable device which can be used to monitor the efficacy of either steam or ethylene oxide sterilization cycles. Hospitals and other health care facilities can thus simplify their inventories of test packs because only one device need be ordered for both types of sterilization monitoring. Although test pack 10 has been described in terms of a tubular shape, those skilled in the art will recognize that any shape which permits the flow of sterilant through a tortuous path dimensioned to promote intimate contact between the sterilant and the moisture absorbent surface of the tortuous path comes within the scope of the instant invention.

For those instances where a health care facility requires only a device to monitor the efficacy of steam sterilization processes alone, an alternative embodiment of the test pack of the present invention, test pack 110, is shown in FIGS. 17 through 19. Where only a device to monitor the efficacy of ethylene oxide sterilization cycles is required, the alternate embodiment of the test pack, 210 shown in FIG. 20 may be employed. Test pack 110 is similar to test pack 10 except that its housing need not include the hole 42 in end 26. In steam sterilization cycles, the optional opening for direct entry of sterilant is not necessary. Test pack 210 is similar to test pack 10 except that it does not include the tab 44 over hole 42. Ethylene oxide in Tables I & II and FIGS. 13 and 14 are applicable to test pack 210. Steam data in Tables III and IV and FIGS. 15 and 16 are applicable to test pack 110.

Test packs 110 and 210 may be constructed exactly the same as test pack 10. Referring to FIGS. 17 through 20, however, the preferred embodiment of test packs 110 and 210 include a housing 112 which is comprised of two end sections, 114 and 116, and a midsection 118 positioned between the end sections 114, 116. Each end section 114, 116 includes a closed end 128, an outer member, or tube 120 and an inner member, or tube, 130. In test pack 210, there is a hole 242 in one of the closed ends 128. The inner tube 130 of each end section 114, 116 may, as shown in the FIGS., telescope into the full depth of its associated outer tube 120. The inner tubes 130 also telescope part way into the opposing open ends, 122 and 124, of midsection 118.

The open ends 122, 124 of midsection 118 are preferably in substantially abutting relationship to the open end of each outer tube 130 of each end section 114, 116 to define seams, or gaps 140 and 142, there between. However, the open ends need not touch.

As with test pack 10, there is a relatively close tolerance between the inner tubes 130 and the outer tubes 120 and midsection 118 so that two tortuous paths for entry of the steam sterilant into housing 112 are defined which progress through the seams 140, 142, the outer surface of the inner tubes 130 and the inner surface of midsection 118. If the inner tubes 130 do not extend into the full depth of the outer tubes 120, a path for entry of the sterilant into housing 112 is also defined between the outer surface of inner tubes 130 and the inner surface of outer tubes 120. In the test pack 210, ethylene oxide sterilant also enters through the second path of entry, hole 242.

When the inner tubes 130 extend into the full depth of outer tubes 120 to meet closed ends 128, the flow of sterilant into housing 112 is prevented. The outer surfaces of inner tubes 130 are preferably smooth to permit an easy sliding contact between the interior of midsection 118 and the exterior of inner tubes 130. The smooth surface aids in assembly and disassembly but is not otherwise required.

Midsection 118 is preferably made of a transparent plastic material which is impermeable to the sterilant and to microorganisms but which permits observation into the interior of housing 112 for viewing the biological indicator 60. Although the entire midsection 118 is shown as being transparent, only a portion of housing 112 need be transparent for observation purposes.

End sections 114, 116 are constructed of the same fiberboard or cellulosic material used for the construction of upper and lower portions 22, 24 of test pack 10. The material used for the construction of end sections 114, 116 has the same properties as the material used for the construction of upper and lower portions 22, 24. End sections 114, 116 therefore, function in the same manner as upper and lower portions 22, 24. As with test pack 10, the outer surfaces of outer tubes 120 may be lined with foil or any other suitable means for making the outer tubes 120 nonabsorbent and impervious to sterilant penetration. The sterilant permeable layer 36, discussed above with respect to test pack 10, preferably covers the exterior of outer tubes 120 of each end section 114, 116, the seams 140, 142 and a portion of the exterior of midsection 118. In this way, sterilant enters housing 112 of test pack 110 only through seams 140 and 142 and the tortuous paths which follow. Sterilant enters housing 112 of test pack 210 additionally through hole 242.

Test packs 110 and 210 include a biological indicator 60 and the means 50 for maintaining the position of biological indicator 60 within housing 112. Biological indicator 60, however, need only carry spores which are known to be highly resistant to either steam or ethylene oxide sterilization cycles depending on the intended application.

Test packs 110 and 210 of the present invention are structured to provide the same advantage for monitoring the efficacy of steam or ethylene oxide respectively sterilization cycles as those provided for monitoring both steam and ethylene oxide sterilization cycles offered by test pack 10.

What is claimed is:

1. A device for monitoring the efficacy of sterilization cycles wherein steam is the sterilant comprising:
  a housing having an interior, at least a portion of said interior being made of a material having heat sink, insulating and moisture absorbent properties, said housing being configured to define at least one tortuous path for entry of sterilant into said housing, said tortuous path having a moisture absorbent surface and being dimensioned to promote intimate contact between said sterilant and said surface as said sterilant moves along said tortuous path; and
  a biological indicator within said housing which includes a calibration of microbes which are resistant to sterilization by steam.

2. The device recited in claim 1 wherein said housing includes a transparent section to permit observation of said biological indicator.

3. The device recited in claim 1 wherein said housing includes two said tortuous paths.

4. The device recited in claim 3 wherein said housing has two end sections and a midsection positioned between said end sections, said midsection having two open ends, each said end section having an inner member and an outer member, each said outer member having an open end in a substantially abutting relationship with one of said open ends of said midsection to define a seam therebetween; and said inner member of each said end section telescopes into the associated said outer member and into a portion of said midsection through said open ends of said midsection past said seam to define said tortuous path progressing through said seam, between the outer surface of said inner member and the inner surface of said portion of said midsection and into said housing.

5. The device recited in claim 1 further comprising a means for positioning said biological indicator within said housing.

6. The device recited in claim 5 wherein said positioning means is a carrier having a cutout section for holding said biological indicator.

7. The device recited in claim 6 wherein said carrier further comprises shock absorbing means at the ends of said carrier.

8. The device recited in claim 1 wherein said biological indicator comprises:
an ampule having one open end;
a cap for covering said open end of said ampule, said cap dimensioned to define an annular space between the interior of said cap and the exterior of said ampule to provide an additional tortuous path for entry of sterilant into said ampule, said cap having two positions, one said position permitting entry of sterilant through said additional tortuous path and the other said position closing said ampule;
a substrate innoculated with a calibration of bacterial spores resistant to sterilization by steam; and
an enclosed frangible vial of growth media for said spores.

9. The device recited in claim 1 wherein said portion of said housing is made from a cellulosic material.

10. A device for monitoring the efficacy of sterilization cycles wherein ethylene oxide is the sterilant comprising:
a housing having an interior, at least a portion of said interior being made of a material having heat sink, insulating, ethylene oxide and moisture absorbent properties, said housing being configured to define at least one tortuous path for entry of sterilant into said housing, said tortuous path having a moisture and ethylene oxide absorbent surface and being dimensioned to promote intimate contact between said sterilant moves along tortuous path;
said housing having a second path of entry into said housing; and
a biological indicator within said housing which includes a calibration of microbes which are resistant to sterilization by ethylene oxide.

11. The device recited in claim 10 wherein said housing includes a transparent section to permit observation of said biological indicator.

12. The device recited in claim 10 wherein said housing includes two said tortuous paths.

13. The device recited in claim 12 wherein said housing has two end sections and a midsection positioned between said end sections, said midsection having two open ends, each said end section having an inner member and an outer member, each said outer member having an open end in a substantially abutting relationship with one of said open ends of said midsection to define a seam therebetween; and
said inner member of each said end section telescopes into the associated said outer member and into a portion of said midsection through said open ends of said midsection past said seam to define said tortuous path progressing through said seam, between the outer surface of said inner member and the inner surface of said portion of said midsection and into said housing.

14. The device recited in claim 10 further comprising a means for positioning said biological indicator within said housing.

15. The device recited in claim 14 wherein said positioning means is a carrier having a cutout section for holding said biological indicator.

16. The device recited in claim 15 wherein said carrier further comprises shock absorbing means at the ends of said carrier.

17. The device recited in claim 10 wherein said biological indicator comprises:
an ampule having one open end;
a cap for covering said open end of said ampule, said cap dimensioned to define an annular space between the interior of said cap and the exterior of said ampule to provide an additional tortuous path for entry of sterilant into said ampule, said cap having two positions, one said position permitting entry of sterilant through said additional tortuous path and the other said position closing said ampule;
a substrate innoculated with a calibration of bacterial spores resistant to sterilization by ethylene oxide; and
an enclosed frangible vial of growth media for said spores.

18. The device recited in claim 10 wherein said portion of said housing is made from a cellulosic material.

* * * * *

UNITED STATES PATENT AND TRADEMARK OFFICE
CERTIFICATE OF CORRECTION

PATENT NO. : 4,914,034

DATED : April 3, 1990

INVENTOR(S) : Jon D. Welsh and Denis G. Dyke

It is certified that error appears in the above-identified patent and that said Letters Patent is hereby corrected as shown below:

Cover page, under References Cited, delete "Hewshrlwood" and substitute therefor --Henshilwood--.

Col. 1, line 23, delete "stain" and substitute therefor --strain--.

Col. 3, line 6, delete "o" and substitute therefor --of--.

Col. 9, line 61, delete "!30" and substitute therefor --130--.

UNITED STATES PATENT AND TRADEMARK OFFICE
CERTIFICATE OF CORRECTION

PATENT NO. : 4,914,034
DATED : April 3, 1990
INVENTOR(S) : Jon D. Welsh and Denis G. Dyke It is certified that error appears in the above-identified patent and that said Letters Patent is hereby corrected as shown below:

Col. 3, line 40, delete "recommenced" and substitute therefor --recommended--.

Col. 7, line 66, delete "$\sim$" and substitute therefor --$\overset{O}{\sim}$--.

Col. 8, line 14, delete "$\sim$" and substitute therefor --$\overset{O}{\sim}$--.

Col. 8, line 31, delete "$\sim$" and substitute therefor --$\overset{O}{\sim}$--.

Col. 8, line 45, delete "$\sim$" and substitute therefor --$\overset{O}{\sim}$--.

Col. 9, line 46, delete "there between" and substitute therefor --therebetween--.

Signed and Sealed this

Twelfth Day of May, 1992

Attest:

DOUGLAS B. COMER

*Attesting Officer*  *Acting Commissioner of Patents and Trademarks*